United States Patent [19]

Buchel et al.

[11] 3,981,885
[45] Sept. 21, 1976

[54] 2-ALKYL-PHENYLHYDRAZONOMIDAZOLENINES

[75] Inventors: Karl Heinz Buchel, Wuppertal-Elberfeld; Paul-Ernst Frohberger; Hans Scheinpflug, both of Leverkusen; Edgar Enders, Cologne, all of Germany

[73] Assignee: Bayer Aktiengesellschaft, Leverkusen, Germany

[22] Filed: July 24, 1975

[21] Appl. No.: 598,604

Related U.S. Application Data

[63] Continuation-in-part of Ser. No. 261,828, June 12, 1972, Pat. No. 3,925,551.

[30] Foreign Application Priority Data

June 15, 1971 Germany............................ 2129524

[52] U.S. Cl.................................. 260/309; 260/157; 424/273
[51] Int. Cl.². ....................................... C07D 233/88
[58] Field of Search............................ 260/309, 157

[56] References Cited
UNITED STATES PATENTS

| | | | |
|---|---|---|---|
| 2,883,373 | 4/1959 | Bossard et al. | 260/157 |
| 3,102,879 | 9/1963 | Baumann et al. | 260/157 |

OTHER PUBLICATIONS

Komatsu et al., I. Chem. Abst., 1971, vol. 74, No. 65540y.

Komatsu et al., II. J. Chem. Soc. (Japan) Ind. Chem. Sec., 1970, vol. 73, pp. 989–991.

Fargher et al., J. Chem. Soc. (London), 1919, vol. 115, p. 256.

*Primary Examiner*—Natalie Trousof
*Attorney, Agent, or Firm*—Burgess, Dinklage & Sprung

[57] ABSTRACT

2-Alkyl-phenylhydrazonoimidazolenines of the formula

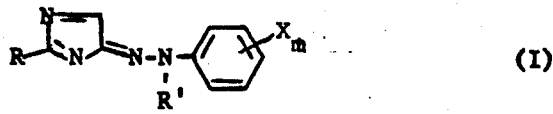

(I)

in which
  R' is hydrogen, alkylcarbonyl, alkoxycarbonyl, arylcarbonyl, aryloxycarbonyl, alkylsulfonyl and optionally substituted arylsulfonyl,
  X is halogen, alkyl, haloalkyl, alkoxy, alkylthio, alkylamino, dialkylamino or nitro, and
  a. R is alkyl of up to 16 carbon atoms, and $m$ is 1 to 4, or
  b. R is alkyl of 2 to 16 carbon atoms, and $m$ is 0 to 4, which possess fungicidal, bactericidal, microbicidal, insecticidal and acaricidal properties.

3 Claims, No Drawings

2-ALKYL-PHENYLHYDRAZONOMIDAZOLENINES

This application is a continuation-in-part of application Ser. No. 261,828, filed June 12, 1972, now U.S. Pat. 3,925,551.

The present invention relates to and has for its objects the provision of particular new 2-alkyl-phenylhydrazonoimidazolenines which possess fungicidal, bactericidal, microbicidal, insecticidal and acaricidal properties. The invention also covers mixtures of such compounds with solid and liquid dispersible carrier vehicles, and methods for producing such compounds and for using such compounds in a new way especially for combating pests, e.g. fungi, bacteria, microbes, insects and acarids, especially fungi and bacteria, with other and further objects becoming apparent from a study of the within specification and accompanying examples.

It is known that zinc ethylene-1,2-bis-dithiocarbamate is effective as a protective leaf fungicide. It is used for the control of potato blight, of brown rot of tomatoes, of fruit scab; banana leaf spot and mildew diseases. Furthermore, it is in use as a seed dressing and soil-treatment agent. It is disadvantageous that zinc ethylene-1,2-bis-dithiocarbamate when applied in small amounts and low concentrations shows only a very slight effect, since it does not become effective until it degrades into volatile substances, such as isocyanates (see R. Wegler, Chemie der Pflanzenschutz- und Schadlings-bekampfungsmittel, Volume 2, pages 6–7 (1970); Springer-Verlag, Berlin). Moreover, its effectiveness against fungal diseases of rice is inadequate.

Fargher et al. in J. Chem. Soc. (London) Vol. 115 (1919) at page 256 disclose:
2-methyl-4-phenylhydrazonoimidoazolenine (70), and 2-methyl-4-p-bromophenylhydrazonoimidoazolenine (71), but no utility therefor is recited.

The present invention provides pesticidal compositions comprising the phenylhydrazonoimidazolenines of the formula

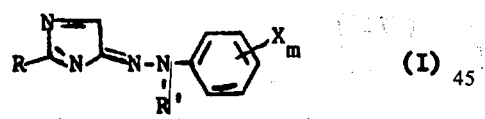

(I)

in which

R' is hydrogen, alkylcarbonyl, alkoxycarbonyl, arylcarbonyl, aryloxycarbonyl, alkylsulfonyl and optionally substituted arylsulfonyl, X is halogen, alkyl, haloalkyl, alkoxy, alkylthio, alkylamino, dialkylamino or nitro, and a. R is alkyl of up to 16 carbon atoms, and $m$ is 1 to 4, or b. R is alkyl of 2 to 16 carbon atoms, and $m$ is 0 to 4, which compositions exhibit excellent fungicidal, and bactericidal properties as well as microbicidal, insecticidal and acaricidal properties.

When formula (I) is employed herein and in the appended claims and when R' is hydrogen it is also intended to embrace the tautomer

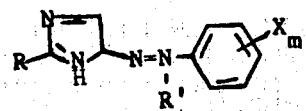

Surprisingly, the new 2-substituted phenylhydrazonoimidazolenines according to the present invention show a considerably better and broader fungitoxic effectiveness than zinc ethylene-1,2-bis-dithiocarbamate and the compounds of Fargher et al which are known from the prior art. The compounds of this invention therefore represent an enrichment of the art.

In the formula (I), it is preferred that R should be straight-chain or branched alkyl with up to 6 carbon atoms, especially lower alkyl such as methyl, ethyl, n-propyl, n-butyl, isopropyl or tert.-butyl; that R' should be hydrogen, an alkylcarbonyl, alkoxycarbonyl or alkylsulfonyl radical wherein the alkyl moiety contains from 1 to 6 carbon atoms, lower alkyl such as methyl, ethyl and isopropyl being especially preferred; or an arylcarbonyl, aryloxycarbonyl or arylsulfonyl radical of which the aryl moiety contains 6 to 10 carbon atoms, phenyl being especially preferred, in the case of an arylsulfonyl radical the aryl being optionally substituted, chlorophenyl being an especially preferred substituted aryl radical; that X should be chlorine or bromine, straight-chain or branched alkyl with up to 6 carbon atoms, especially lower alkyl such as methyl, ethyl, propyl, isopropyl or tert.-butyl, alkoxy or alkylthio with, in either case, up to 6 carbon atoms, especially methoxy or ethoxy, alkylamino or dialkylamino (the alkyl radicals of the latter being identical or different) with up to 6 carbon atoms in each alkyl radical, or nitro; and that $m$ should be 0 to 3, especially 1 or 2.

The present invention also provides a process for the preparation of a 2-substituted phenylhydrazonoimidazolenine of the formula (I) in which a. an imidazole of the general formula

(II)

in which

R has the meaning stated above, is reacted with a diazonium salt of the general formula

(III)

in which

X, Y, $m$ and $n$ have the meanings stated above, in the presence of an acid-binding agent and optionally in the presence of a diluent, or b. a phenylhydrazonoimidazolenine salt of the general formula

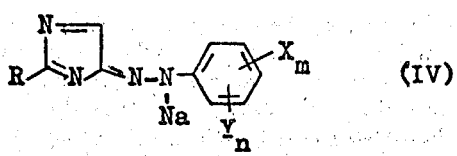

in which

R, X, Y, *m* and *n* have the meanings stated above, is reacted with an acid chloride, chloroformic acid ester or sulfonic acid ester chloride of the general formula

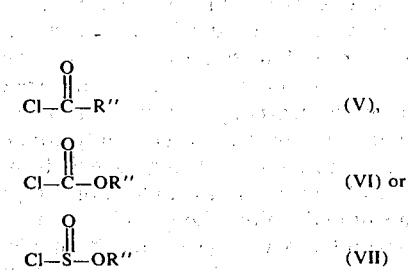

in which

R'' is alkyl or aryl, or in formula (V) optionally substituted aryl, optionally in the presence of a diluent.

If 2-isopropylimidazole and phenyldiazonium chloride are used as starting materials in process variant (a), the reaction course can be represented by the following equation:

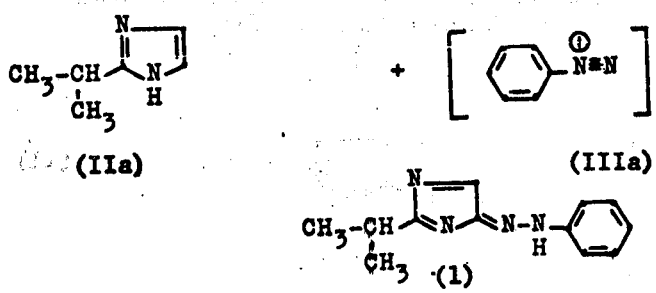

If the sodium salt of 2-isopropyl-4-phenylhydrazonoimidazolenine and chloroformic acid methyl ester are used as starting materials in process variant (b), the reaction course can be represented by the following equation:

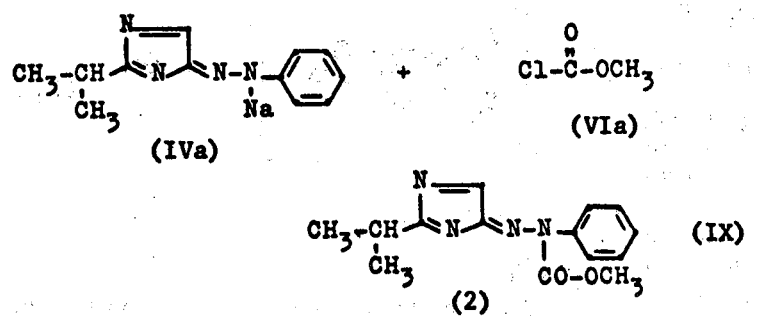

The imidazoles (II) that are used as starting materials are known.

A number of phenyldiazonium salts (III) to be used as starting materials are known. Those that have not hitherto been described in the literature can be prepared by methods analogous to the methods used to prepare the known ones (see Houben-Weyl, Methoden der Organischen Chemie, Volume 10/3, Georg-Thieme-Verlag, Stuttfart, page 514 [1965]), as described in Example 1 hereinbelow.

The phenylhydrazonoimidazolenine salts of the formula (IV) to be used as starting materials have not yet been described in the prior art; as exemplified hereinbelow, they can be prepared by reacting 2-substituted phenylhydrazonoimidazolenines of the formula (I), in which R' is hydrogen, with equivalent amounts of sodium ethylate.

The acid chlorides (V), chloroformic acid esters (VI) and sulfonic acid ester chlorides (VII) to be used as starting materials are known.

When carrying out process variant (a) according to the invention, in general a diluent is used. Especially suitable for this purpose are aqueous solvents or aqueous solvent mixtures. The reaction is, however, preferably carried out in water.

As the acid-binding agent, any usual acid-binder may be used, especially an alkali metal hydroxide, such as sodium hydroxide; an alkali metal carbonate, such as sodium carbonate or potassium carbonate; an alkaline earth metal hydroxide, such as calcium hydroxide; or an alkaline earth metal carbonate, such as calcium carbonate. Sodium carbonate is particularly suitable.

The reaction temperatures in process variant (a) can be varied within a fairly wide range. In general, the work is carried out at from about −20°C to +20°C, preferably from about −5°C to +5°C.

When carrying out process variant (a), there are used, in general, equimolar amounts of the starting materials. Deviation from the stoichiometric proportion is possible, but brings no substantial improvement of yield.

To isolate the compounds of the formula (I) that are prepared according to process variant (a), it suffices to filter them out of the reaction mixture, since they are obtained in crystalline form. They are purified by recrystallization.

As a diluent in process variant (b), all inert organic solvents are suitable. Preferred solvents are hydrocarbons, such as petroleum ether, benzene, toluene or xylene; ethers, such as dioxane or tetrahydrofuran; nitriles, such as acetonitrile or benzonitrile; alcohols, such as ethyl alcohol, isopropyl alcohol or butyl alcohol; or halogenated hydrocarbons, such as methylene chloride or chloroform.

The reaction temperatures in process variant (b) can also be varied within a farily wide range. In general, the work is carried out at from about −20°C to +50°C, preferably at from about −5°C to +40°C.

When carrying out process variant (b) there are used, in general, between 1.1 and 1.5 moles of the compound of the formula (V), (VI) or (VII) per mole of the compound of the formula (IV). Further exceeding of the stoichiometric amount brings no substantial improvement of yield.

To isolate the compounds of the formula (I) that are obtained according to process variant (b), the solvent is distilled off in a vacuum and the residue is digested with an organic solvent; the compounds of the formula (I) go into solution, while the sodium chloride also formed remains undissolved. The yellow and orange-red colored products so obtained are purified by recrystallization.

The active compounds according to the invention exhibit a strong fungicidal activity. In the concentrations necessary for the control of fungi they do not damage cultivated plants and they have a low toxicity to warm-blooded animals. For these reasons, they are suitable for use as crop protection agents for the control of fungi. Fungicidal agents in crop protection are used for the control of Archimycetes, Phycomycetes, Ascomycetes, Basidiomycetes and Fungi Imperfecti.

The active compounds according to the invention have a very broad activity spectrum and can be applied against parasitary fungi that infect above-the-soil parts of plants or attack the plants from the soil, and seed-borne pathogenic fungi.

The active compounds according to the invention have given good results particularly in the control of rice diseases. Thus, they have shown an excellent activity against the fungi *Piricularia oryzae* and *Pellicularia sasakii*, by reason of which they can be used for the joint control of these two diseases. That means a substantial advance, since up to now agents of different chemical constitution have generally been used against these two fungi. Surprisingly, the active compounds show not only a protective activity, but also a curative effect.

The active compounds are likewise highly effective and of particular practical importance when they are used as seed dressings or soil-treatment agents against phytopathogenic fungi that adhere to the seed or occur in the soil and cause, in cultivated plants, seedlings diseases, root rots, tracheomycoses and stem, stalk, leaf, blossom, fruit or seed diseases, such as *Tilletia caries*, *Helminthosporium gramineum*, *Fusarium nivale*, *Fusarium culmorum*, *Rhizoctonia solani*, *Phialophora cinerescens*, *Verticillium alboatrum*, *Fusarium dianthi*, *Fusarium cubense*, *Fusarium oxysporum*, *Fusarium solani*, *Sclerotinia sclerotiorum*, *Thielaviopsis basicola* and *Phytophthora cactorum*.

The active compounds according to the invention have, for instance, also proved effective against *Cochliobolus miyabeanus*, *Mycosphaerella musicola*, *Cercospora personata*, *Botrytis cinerea* and *Alternaria* species.

Phytopathogenic bacteria species, such as *Xanthomonas oryzae*, can also be controlled.

Furthermore, the active compounds according to the invention are also effective as leaf fungicides; they can for example be used with success against *Erysiphe* and *Fusicladium* species.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methylisobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, bactericides, microbicides, insecticides and acaricides, or rodenticides, nematocides, herbicides, fertilizers, growth-regulating agents, etc. if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

In the case of seed treatment, there are required, in general, amounts of active compound of 0.1 to 10 g, preferably 0.5 to 5 g, per kg of seed. For soil treatment, amounts of active compound of 1 to 500 g, preferably 10 to 200 g, per cubic meter of soil are generally required.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi, bacteria, microbes, insects and acarids and more particularly methods of combating at least one of insects, fungi and bacteria, which comprises applying to at least one of correspondingly (a) such insects, (b) such acarids, (c) such fungi, (d) such bacteria, (e) such microbes, and (f) the corresponding habitat thereof, i.e. the locus to be protected, a correspondingly combative or toxic amount, i.e. insecticidally, acaricidally, fungicidally, bactericidially or microbicidally effective amount, of the particular active compound of the invention alone or together with a carrier vehicle as noted above. The instant formulations or compositions are applied in the usual manner for instance by spraying, atomizing, vaporizing, scattering, dusting, watering, squirting, sprinkling, pouring, fumigating, It will be realized, of course, that the concentration of the particular active compound utilized in admixture with the carrier vehicle will depend upon the intended appliciation. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

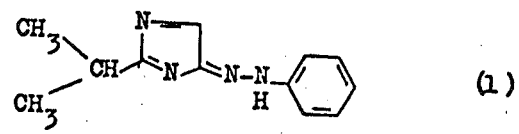

27.7 g (0.25 mole) of 2-isopropylimidazole and 100 g of sodium carbonate are stirred into a mixture of 1.5 kg of ice and 1.5 liters of water. While this is being done, an aqueous phenyldiazonium chloride solution, which had beforehand been prepared from 23.3 g (0.25 mole) of aniline, 17.2 g (0.25 mole) of sodium nitrite and 250 ml of 2.5%-strength hydrochloric acid at 0°C, is slowly added. There precipitates an orange-yellow sediment. The mixture, after completion of addition of the diazonium salt solution, is stirred for a further 15 minutes; thereafter, the precipitate is filtered off with suction, washed well with water, dried, and recrystallized from benzene. 24 g (44% of theory) of 2-isopropyl-4-phenylhydrazonoimidazolenine of the melting point 168°C are obtained.

EXAMPLE 2

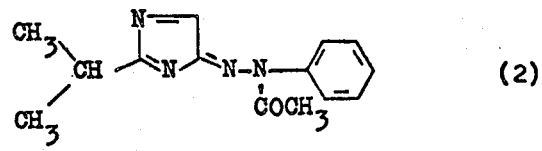

23.6 g (0.1 mole) of sodium 2-isopropyl-4-phenylhydrazonoimidazolenine, which is prepared from 0.1 mole of 2-isopropyl-4-phenylhydrazonoimidazolenine by addition thereto of 0.1 mole of sodium ethylate, is dissolved in 200 ml of anhydrous acetonitrile. 8.6 g (0.11 mole) of acetyl chloride are added dropwise at a temperature of −5°C, with stirring, and further stirring is effected for one hour at 40°C. Thereafter, the solvent is distilled off in a vacuum, the residue is boiled out twice with, in each case, 1 liter of ligroin. 17 g (66% of theory) of 2-isopropyl-4-(N-β-phenyl-β-acetyl)-hydrazonoimidazolenine are obtained as yellow crystals of the melting point 129°C.

EXAMPLE 3

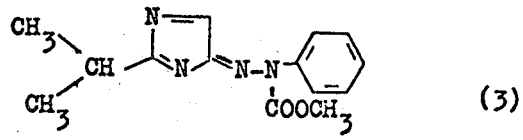

23.6 g (0.1 mole) of sodium 2-isopropyl-4-phenylhydrazonoimidazolenine are dissolved in 250 ml of anhydrous acetonitrile. At a temperature of 0°C, 14.1 g (0.15 mole) of chloroformic acid methyl ester are added dropwise and stirring for 17 hours is effected at room temperature. After the solvent has been distilled off in a vacuum, the residue is digested with methylene chloride, filtration from undissolved sodium chloride being effected. 2-isopropyl-4-(N-β-phenyl-β-methylcarbonyldioxy)-hydrazonoimidazolenine is obtained as orange-red needles which, again recrystallized from ligroin, have a weight of 18.5 g (68% of theory) and a melting point of 116°C.

EXAMPLE 4

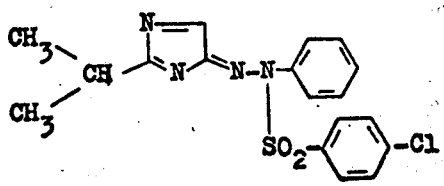 (4)

23.6 g (0.1 mole) of sodium 2-isopropyl-4-phenylhydrazonoimidazolenine are dissolved in 200 ml of anhydrous acetonitrile. At a temperature of 0°C, a solution of 23.2 g (0.11 mole) of p-chlorobenzenesulfochloride in 60 ml of acetonitrile is added dropwise, with stirring, and further stirring is effected at room temperature for one hour. After concentration of the solvent in a vacuum, the residue is recrystallized from 600 ml of ligroin the sodium chloride formed remaining behind undissolved. 28.8 g (74% of theory) of 2-isopropyl-4-[N-β-phenyl-β-(p-chlorophenylsulfonyl)]-hydrazonoimidazolenine of the melting point 137°C are obtained.

EXAMPLE 5

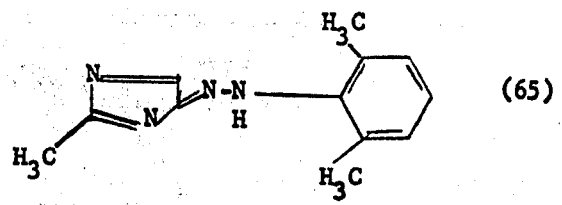 (65)

200 grams (1.65 moles) of 2,6-dimethylaniline are mixed with 500 ml concentrated hydrochloric acid in 2.5 liters of ice water and at a temperature of from −10 to 0°C a solution of 120 grams of sodium nitrite in 600 ml of water is added dropwise. The mass is stirred for an additional half hour and excess nitrite is decomposed through the addition of amidosulfonic acid. The diazo solution is added dropwise at 0° to 5°C to 250 g (3.04 moles corresponding to an 85% excess) of 2-methylamidazole in 2.5 liters of water containing 250 g of potassium carbonate. Thereafter 10% sodium hydroxide solution is added dropwise until a pH of 9 to 10 is reached. When no further diazotized aniline is visible, 50% acetic acid is added dropwise to neutrality. Thereafter the precipitated product is sucked off, washed salt-free with water and dried in air. There are obtained 360 grams of crude monohydrate of 2-methyl-4-(2′,6′-dimethylphenylhydrazono)-imidazolenine, whose melting point is 98°–100°C. By recrystallization in benzene there are obtained 300 grams of a water-free crystalline compound having a melting point of 167°–169°C (with decomposition). The yield of pure material is 85% of theory.

The compounds specified in the following Table are prepared by methods analogous to those given in the foregoing Examples:

Table 1

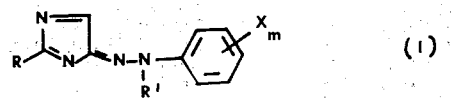 (1)

| Compound Number | R | R' | X | m | Melting point °C |
|---|---|---|---|---|---|
| 5 | $CH_3$ | H | 3′,5′-$CF_3$ | 2 | 199 |
| 6 | $CH_3$ | H | 2′-Cl-5′-$CF_3$ | 2 | 205–212 decomp. |
| 7 | $CH_3$ | H | 4′-Cl | 1 | 198 |
| 8 | $CH_3$ | H | 2′-Cl | 1 | 181 |
| 9 | $CH_3$ | H | 3′,5′-Cl | 2 | 188 decomp. |
| 10 | $CH_3$ | H | 4′-$NO_2$ | 1 | 192–196 decomp. |
| 11 | $CH_3$ | H | 4′-$OC_2H_5$ | 1 | 183–187 |
| 12 | $C_2H_5$ | H | 3′-Cl-4′-$CF_3$ | 2 | 129–132 decomp. |
| 13 | $C_2H_5$ | H | 3′,5′-$CF_3$ | 2 | 162 decomp. |
| 14 | $C_2H_5$ | H | — | 0 | 184–186 |
| 15 | $C_2H_5$ | H | 2′-Cl | 1 | 179 decomp. |
| 16 | $C_2H_5$ | H | 4′-$NO_2$ | 1 | 175–177 |
| 17 | $C_2H_5$ | H | 4′-$OC_2H_5$ | 1 | 202–204 |
| 18 | $C_3H_7$ | H | — | 0 | 146 |
| 19 | $C_3H_7$ | H | 2′-Cl | 1 | 151–156 decomp. |
| 20 | $C_3H_7$ | H | 4′-$NO_2$ | 1 | 146–148 decomp. |
| 21 | $C_3H_7$ | H | 4′-$OC_2H_5$ | 1 | 132–134 |
| 22 | $CH(CH_3)_2$ | H | 4′-$C(CH_3)_3$ | 1 | 186–188 |
| 23 | $CH(CH_3)_2$ | H | 2′-Cl | 1 | 178–180 decomp. |
| 24 | $CH(CH_3)_2$ | H | 4′-$NO_2$ | 1 | 188–189 decomp. |
| 25 | $CH(CH_3)_2$ | H | 2′-Cl-5′-$CF_3$ | 2 | 171–172 decomp. |
| 26 | $CH(CH_3)_2$ | H | 4′-$OC_2H_5$ | 1 | 187–189 decomp. |
| 27 | $CH(CH_3)_2$ | H | 2′-$OCH_3$-4′,5′-Cl | 2 | 191–192 decomp. |
| 28 | $CH(CH_3)_2$ | H | 3′-$OC_2H_5$ | 1 | 194–195 decomp. |
| 29 | $CH(CH_3)_2$ | H | 2′-$OC_2H_5$ | 1 | 176–178 |
| 30 | $CH(CH_3)_2$ | H | 3′,5′-$CH_3$ | 2 | 188–190 |

Table 1-continued

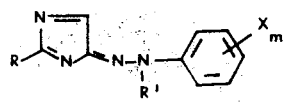 (1)

| Compound Number | R | R' | X | m | Melting point °C |
|---|---|---|---|---|---|
| 31 | CH(CH₃)₂ | H | 4'-OCH₃ | 1 | 153–154 |
| 32 | CH(CH₃)₂ | H | 3'-OCH₃ | 1 | 192–193 |
| 33 | CH(CH₃)₂ | H | 2'-OCH₃-5'-CH₃ | 2 | 197–198 |
| 34 | CH(CH₃)₂ | H | 3',5'-CF₃ | 2 | 201–202 |
| 35 | CH(CH₃)₂ | H | 2'-OC₂H₅-5'-CH₃ | 2 | 189–190 |
| 36 | CH(CH₃)₂ | H | 3'-OCH₃-4'-CH₃ | 2 | 175–177 |
| 37 | CH(CH₃)₂ | H | 2',4'-CH₃ | 2 | 177–178 |
| 38 | CH(CH₃)₂ | H | 3'-NO₂-4'-CH₃ | 2 | 187–188 |
| 39 | CH(CH₃)₂ | H | 4'-CH₃ | 1 | 167–168 |
| 40 | CH(CH₃)₂ | H | 4'-C₂H₅ | 1 | 168–170 |
| 41 | CH(CH₃)₂ | H | 2',5'-OC₂H₅ | 2 | 168–171 |
| 42 | CH(CH₃)₂ | H | 2',4'-Cl | 2 | 183 |
| 43 | CH(CH₃)₂ | H | 3',5'-Cl | 2 | 188 |
| 44 | CH(CH₃)₂ | H | 2'-CH(CH₃)₂ | 1 | 143–146 |
| 45 | CH(CH₃)₂ | COCH₃ | 2'-Cl | 1 | 139–143 |
| 46 | CH(CH₃)₂ | COOCH₃ | 2'-Cl | 1 | 159 |
| 47 | CH(CH₃)₂ | COCH₃ | 2'-Cl-5'-CF₃ | 2 | 159–161 |
| 48 | CH(CH₃)₂ | COOCH₃ | 2'-Cl-5'-CF₃ | 2 | 112–115 |
| 49 | CH(CH₃)₂ | COCH₃ | 4'-OC₂H₅ | 1 | 128 |
| 50 | CH(CH₃)₂ | COOCH₃ | 4'-OC₂H₅ | 1 | 140–142 |
| 51 | CH(CH₃)₂ | COCH₃ | 3',5'-CF₃ | 2 | 120–124 |
| 52 | CH(CH₃)₂ | COOCH₃ | 3',5'-CF₃ | 2 | 142 |
| 53 | CH(CH₃)₂ | COCH₃ | 3',5'-CF₃ | 2 | 101 |
| 54 | CH(CH₃)₂ | COOCH₃ | 3',5'-CH₃ | 2 | 128–131 |
| 55 | CH(CH₃)₂ | COOCH—(CH₃)₂ | — | 0 | 102–104 |
| 56 | CH(CH₃)₂ | CO—C₆H₅ | — | 0 | 144–146 |
| 57 | CH(CH₃)₂ | CO—C₆H₅ | 4'-OC₂H₅ | 1 | 114–116 |
| 58 | CH(CH₃)₂ | COOCH—(CH₃)₂ | 4'-OC₂H₅ | 1 | 106–107 |
| 59 | CH(CH₃)₂ | COO—C₆H₅ | — | 0 | 148 |
| 60 | CH(CH₃)₂ | COCH₃ | 4'-C(CH₃)₃ | 1 | 136–139 |
| 61 | CH(CH₃)₂ | COOCH₃ | 4'-C(CH₃)₃ | 1 | 121–123 |
| 62 | CH(CH₃)₂ | SO₂CH₃ | — | 0 | 140–143 |
| 63 | CH₃ | H | 2'6'-Cl | 2 | 207 |
| 64 | CH₃ | H | 2'-Cl-6'-CH₃ | 2 | 160–161 |
| 66 | CH(CH₃)₂ | H | 2,6-(CH₃)₂-5-NO₂ | 3 | 201 |
| 67 | CH(CH₃)₂ | H | 2,6-(CH(CH₃)₂)₂-4-NO₂ | 1 | 190 |
| 68 | CH(CH₃)₂ | H | 2,6-(CH₃)₂-4-NO₂ | 3 | 238 |
| 69 | CH(CH₃)₂ | H | 2,6-Cl₂ | 2 | 226 |
| 70 | CH₃ | H | — | 0 | 158 |

Other compounds in accordance with the present invention include:
2-isopropyl-4-(p-methylthiophenylhydrazono)-imidazolenine,
2-ethyl-4-(p-methylthiophenylhydrazono)-imidazolenine,
2-ethyl-4-(p-dimethylaminophenylhydrazono)-imidazolenine, and the like.

The activities of the compounds synthesized hereinabove are shown in the following biological tests.

EXAMPLE 6

Agar Plate Test

Test for fungitoxic effectiveness and breadth of the activity spectrum.

Solvent: Acetone
Parts by weight: (a) 1000 (b) 100

To produce a suitable preparation of the active compound, 1 part by weight of the active compound is taken up in the stated amount of solvent.

To potato dextrose agar which has been liquefied by heating there is added the preparation of the active compound in such an amount that the desired concentration of active compound is set up therein. After thorough shaking to achieve a uniform dispersion of the active compound, the agar is poured into Petri dishes under sterile conditions. When the mixture of substrate and active compound has solidified, test fungi from pure cultures are inoculated on to it in small discs of 5 mm diameter. The Petri dishes remain at 20°C for 3 days for incubation.

After this time, the inhibiting action of the active compound on the mycelium growth is determined, in categories, taking into account the untreated control. 0 means no mycelium growth, either on the treated substrate or on the inoculum; the symbol — means mycelium growth on the inoculum only, no spread to the treated substrate; and the symbol + means mycelium growth from the inoculum on to the treated substrate, similar to the spread to the untreated substrate of the control.

The active compounds, the concentration of the active compounds, the test fungi and the inhibition effects achieved can be seen from the following Table:

EXAMPLE 7

Mycelium Growth Test

Nutrient medium used:
20 parts by weight agar-agar
200 parts by weight potato decoction
5 parts by weight malt
15 parts by weight dextrose
5 parts by weight peptone
2 parts by weight disodium phosphate
0.30 part by weight calcium nitrate Proportion of solvent mixture to nutrient medium:
2 parts by weight solvent mixture
100 parts by weight agar nutrient medium.
Composition of solvent mixture:
0.19 part by weight dimethyl formamide
0.01 part by weight alkylarylpolyglycol ether
1.80 parts by weight water The amount of active compound required for the desired concentration of active compound in the nutrient medium is mixed with the stated amount of solvent mixture. The concentrate is thoroughly mixed, in the stated proportion, with the liquid nutrient medium (which has been cooled to 42°C) and is then poured into Petri dishes of 9 cm diameter. Control dishes to which the preparation has not been added are also set up.

When the nutrient medium has cooled and solidified, the dishes are inoculated with the species of organisms stated in the Table and incubated at about 21°C.

Evaluation is carried out after 4–10 days, dependent upon the speed of growth of the organisms. When evaluation is carried out, the radial growth of the mycelium on the treated nutrient media is compared with the growth on the control nutrient medium. In the evaluation of the organism growth, the following characteris- Table 2

| | | Agar plate test | | | | | | | | |
|---|---|---|---|---|---|---|---|---|---|---|
| Active compound | | Concentration of active compound in the substrate in mg per liter | Corticium rolfsii | Sclerotinia sclerotiorum | Verticillium alboatrum | Thielaviopsis basicola | Phytophthora cactorum | Fusarium culmorum | Fusarium oxysporum | Fusarium solani f. pisi |
| untreated | | — | + | + | + | + | + | + | + | + |
| 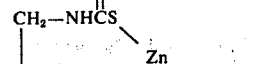 | (known) | a) 10<br>b) 100 | +<br>+ | +<br>+ | +<br>+ | +<br>0 | +<br> | +<br>+ | +<br>+ | +<br>+ |
| 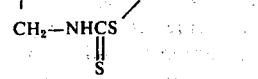 | (known) | b) 100 | 0 | + | + | — | + | + | + | + |
| 7 | | b) 100 | 0 | + | + | 0 | 0 | + | + | + |
| 8 | | b) 100 | + | + | + | 0 | 0 | + | + | + |
| 10 | | b) 100 | + | + | + | — | 0 | + | + | + |
| 12 | | b) 100 | 0 | 0 | + | 0 | 0 | — | + | + |
| 14 | | b) 100 | 0 | — | 0 | 0 | 0 | + | + | + |
| 15 | | b) 100 | 0 | 0 | + | + | — | 0 | + | + |
| 16 | | b) 100 | — | + | + | — | 0 | + | + | + |
| 18 | | a) 10<br>b) 100 | 0<br>0 | +<br>0 | +<br>0 | +<br>0 | +<br>0 | +<br>0 | +<br>+ | +<br>+ |
| 19 | | b) 100 | 0 | + | 0 | — | 0 | + | + | + |
| 1 | | a) 10<br>b) 100 | 0<br>0 | —<br>0 | +<br>+ | +<br>0 | —<br>0 | +<br>+ | +<br>+ | +<br>+ |
| 23 | | b) 100 | 0 | + | + | — | 0 | + | + | + |
| 26 | | b) 100 | 0 | — | + | — | 0 | + | + | + |
| 2 | | a) 10<br>b) 100 | 0<br>0 | —<br>— | +<br>+ | +<br>— | —<br>0 | +<br>+ | +<br>+ | +<br>+ |
| 3 | | b) 100 | — | 0 | + | — | 0 | + | + | + |
| 45 | | b) 100 | 0 | + | + | — | — | + | + | + |
| 30 | | b) 100 | 0 | 0 | — | + | 0 | + | — | + |
| 31 | | a) 10<br>b) 100 | 0<br>0 | +<br>0 | +<br>+ | +<br>+ | 0<br>0 | +<br>+ | +<br>+ | +<br>+ |
| 32 | | b) 100 | 0 | — | + | + | — | + | + | + |
| 36 | | b) 100 | 0 | — | + | + | 0 | + | 0 | + |
| 37 | | b) 100 | 0 | 0 | 0 | + | 0 | + | + | + |
| 39 | | b) 100 | 0 | 0 | + | + | 0 | + | 0 | + | tic values are used:
0 no organism growth
1 very strong inhibition of growth
2 medium inhibition of growth
3 slight inhibition of growth
4 growth equal to that of untreated control.

The active compounds, the concentrations of the active compounds and the results can be seen from the following Table:
liquor is mixed with the stated amount of solvent, and the concentrate is diluted with the stated amount of water containing the stated additives.

2 batches each consisting of 30 rice plants about 2 – 4 weeks old are sprayed with the spray liquor until dripping wet. The plants remain in a greenhouse at temperatures of 22° to 24°C and a relative atmospheric humidity of about 70% until they are dry. One batch of the plants is then inoculated with an aqueous suspension of 100,000 to 200,000 spores/ml of *Piricularia oryzae* and placed in a chamber at 24°–26°C and 100% relative atmospheric humidity. The other batch of the plants is infected with a culture of *Pellicularia sasakii* grown on malt agar and placed at 28° – 30°C and 100% relative atmospheric humidity.

5 to 8 days after inoculation, the infection of all the leaves present at the time of inoculation with *Piricularia oryzae* is determined as a percentage of the un- Table 3

| | | | | | Fungi and bacterium | | | | |
|---|---|---|---|---|---|---|---|---|---|
| cularia Active compound | | | Piricine-oryzae | Phialophora cularia rescens | Pelli-musi-sasakii | Mycosphaerella miyacola | Cochliobolus cofbeanus | Colletotrichum monas feanum | Xanthomonas alboaoryzae | Verticillium trum |
| $CH_3-CH_2-NH-CS-S$<br>$\quad\quad\quad\quad\quad\quad\quad\quad\quad >Zn$ (known)<br>$CH_2-NH-CS-S$ | (A) | 0 | 4 | 3 | 1 | 4 | 4 | 4 | 4 |
| 7 | | 0 | 2 | 2 | 2 | 3 | 1 | — | — |
| 14 | | 0 | 1 | 3 | 1 | 2 | 0 | — | — |
| 18 | | 0 | 0 | — | 0 | 0 | 0 | — | 3 |
| 1 | | 0 | 0 | 1 | 0 | 0 | 0 | 0 | 2 |
| 26 | | 0 | 0 | — | 1 | 2 | 0 | — | — |
| 28 | | 0 | 1 | 3 | 1 | 2 | 0 | — | — |
| 2 | | 0 | 0 | 2 | 0 | 1 | 0 | — | 3 |
| 3 | | 0 | 0 | 3 | 0 | 1 | 0 | — | 3 |
| 30 | | 0 | 3 | — | — | 2 | 0 | — | — |
| 31 | | 0 | 0 | 1 | 0 | 0 | 0 | — | 3 |
| 32 | | 0 | 1 | 3 | — | 2 | 0 | — | — |
| 39 | | 0 | 0 | 1 | 0 | 1 | 0 | — | 3 |
| 49 | | 0 | 0 | — | — | 2 | 0 | — | — |

EXAMPLE 8

Piricularia and Pellicularia Test

Solvent: 1.9 parts by weight dimethyl formamide
Dispersing agent: 0.1 part by weight alkylarylpolyglycol ether
Water: 98 parts by weight The amount of active compound required for the desired concentration of active compound in the spray liquor is mixed with the stated amount of solvent, and the concentrate is diluted with the stated amount of water containing the stated additives.

2 batches each consisting of 30 rice plants about 2 – 4 weeks old are sprayed with the spray liquor until treated but also inoculated control plants. In the case of the plants infected with *Pellicularia sasakii*, the infection on the leaf sheaths after the same time is also determined in proportion to the untreated but infected control. 0% means no infection; 100% means that the infection is exactly as great in the case of the control plants.

The active compounds, the concentrations of the active compounds and the results obtained can be seen from the following Table:

Table 4

| | | | Infection as a percentage of the infection of the untreated control with a concentration of active compound (in % by weight) of | | | |
|---|---|---|---|---|---|---|
| | | | (a) | | (b) | |
| Active compound | | protective = pr.<br>curative = cur. | 0.05 | 0.025 | 0.05 | 0.025 |
| $CH_3-CH_2-NH-CS-S$<br>$\quad\quad\quad\quad\quad\quad\quad >Zn$<br>$CH_2-NH-CS-S$<br>(known) | (A) | pr.<br>cur. | 25<br>100 | 100 | | |
| $CH_3-\underset{N}{\overset{N=}{\bigg\lvert}}\!\!\!\underset{N}{\bigg\rvert}\!\!-N-NH-\bigcirc$ (known) | (B) | pr. | 25 | | 50 | |

Table 4-continued

| Piricularia(a) and Pellicularia(b) test | | | | | |
|---|---|---|---|---|---|
| | | Infection as a percentage of the infection of the untreated control with a concentration of active compound (in % by weight) of | | | |
| Active compound | protective = pr. curative = cur. | (a) | | (b) | |
| | | 0.05 | 0.025 | 0.05 | 0.025 |
| 18 | pr. | 25 | | 0 | 25 |
| 1 | pr. | 0 | 0 | 25 | 75 |
| 26 | pr. | 0 | 0 | | |
| 27 | pr. | 0 | 75 | | |
| 28 | pr. | 0 | | | |
| 2 | pr. | 0 | 0 | | |
| | cur. | 13 | 75 | | |
| 31 | pr. | 0 | 0 | | |
| 36 | pr. | 25 | 25 | | |
| 39 | pr. | 0 | 0 | | |
| | cur. | 25 | | | |
| 49 | pr. | 0 | 0 | | |

EXAMPLE 9

Seed Dressing Test/Bunt of Wheat (Seed-borne Mycosis)

To produce a suitable dry dressing, the active compound is extended with a mixture of equal parts by weight of talc and kieselguhr to give a finely powdered mixture with the desired concentration of the active compound.

Wheat seed is contaminated with 5 g of the chlamydospores of Tilletia tritici per kg of seed. To apply the dressing, the seed is shaken with the dressing in a closed glass flask. The seed, on moist loam under a cover of a layer of muslin and 2 cm of moderately moist compost soil, is exposed to optimum germination conditions for the spores for 10 days at 10°C in a refrigerator.

The germination of the spores on the wheat grains, each of which is contaminated with about 100,000 spores, is subsequently determined microscopically.

The smaller the number of spores which have germinated, the more effective is the active compound.

The active compounds, the concentrations of the active compounds in the dressing, the amounts of dressing used and the percentage spore germination can be seen from the following Table:

Table 5

| Seed dressing test / bunt of wheat | | | |
|---|---|---|---|
| Active compound | Concentration of active compound in the dressing in % by weight | Applied amount of dressing in g/kg seed | Spore germination in % |
| non-dressed | — | — | >10 |
| $\begin{array}{c}CH_2-NHCS\\ \phantom{CH_2-NH}\phantom{C}\\ CH_2-NHCS\end{array}\!\!>\!Zn$ (A) (known) | 10 | 1 | 5 |
| 70 | 10 | 1 | 0.005 |
| 8 | 10 | 1 | 0.05 |
| 10 | 10 | 1 | 0.5 |
| 14 | 10 | 1 | 0.05 |
| 15 | 10 | 1 | 0.05 |
| 18 | 10 | 1 | 0.05 |
| 1 | 10 | 1 | 0.05 |
| 24 | 10 | 1 | 0.5 |
| 2 | 10 | 1 | 0.000 |
| 49 | 10 | 1 | 0.005 |
| 65 | 10 | 1 | 0.000 |
| | 3 | 1 | 0.000 |
| | 1 | 1 | 0.005 |

EXAMPLE 10

Seed Dressing Test/Bunt of Wheat/Field Test (Seed-borne Mycosis)

To produce a suitable dry dressing, the active compound is extended with a mixture of equal parts by weight of talc and kieselguhr to give a finely powdered mixture with the desired concentration of the active compound.

The dressing takes place in 4 individual portions of 100 g, each sown on 4 parcels having a size of 5 m². The percentages of spikes attacked are obtained by completely counting all of the sick spikes on the individual parcels and estimating the total number of all spikes based on counting a few parcels of apparently the same crop density. In order to examine the effect against bunt of wheat (tilettia caries), there is used winter wheat (certified seed material) which was previously contaminated with 2 g of chlamydo spores per each kg of seed material.

Dressing: Beginning Of October
Sowing: October 10 to 20
Evaluation: End of June to middle of July The percentages of the sick spikes are based in each case on about 2000 spikes per parcel — altogether on about 8000 spikes per each test.

Active materials, active material concentrations in the dressing, amount of dressing applied and the percentage of infected spikes based on the total number of spikes formed are set out in the following Table 6:

Table 6

Seed dressing test / bunt of wheat field test

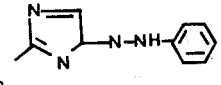

It will be appreciated that the instant specification and examples are set forth by way of illustration and not limitation, and that various modifications and changes may be made without departing from the spirit and scope of the present invention.

What is claimed is:

1. A 2-substituted phenylhydrazonoimidazolenine of the formula

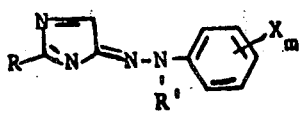

in which

R' is alkylcarbonyl, alkoxycarbonyl or alkylsulfonyl wherein the alkyl or alkoxy moiety contains from 1 to 6 carbon atoms; or arylcarbonyl, aryloxycarbonyl or optionally chlorine substituted arylsulfonyl wherein the aryl moiety contains 6 to 10 carbon atoms, X is halogen, nitro, or alkyl, haloalkyl, alkoxy, alkythio, alkylamino or dialkylamino wherein the alkyl or alkoxy moiety contains up to 6 carbon atoms, and a. R is alkyl of up to 16 carbon atoms, and $m$ is 1 to 4, or b. R is alkyl of 2 to 16 carbon atoms, and $m$ is 0 to 4.

2. A compound according to claim 1 wherein R has up to 6 carbon atoms, and X is chlorine, bromine, nitro, or alkyl, haloalkyl, alkoxy, alkylthio, alkylamino or dialkylamino with up to 6 carbon atoms in each alkyl group.

3. A compound according to claim 2 wherein X is chlorine, bromine, nitro, alkyl or alkoxy of up to 4 carbon atoms or trifluoromethyl.

* * * * *